United States Patent
Speier et al.

(10) Patent No.: US 6,844,728 B2
(45) Date of Patent: Jan. 18, 2005

(54) PRECONDITIONING SPINS NEAR A NUCLEAR MAGNETIC RESONANCE REGION IN A BOREHOLE

(75) Inventors: Peter Speier, Stafford, TX (US); Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/197,780

(22) Filed: Jul. 18, 2002

(65) Prior Publication Data

US 2003/0020473 A1 Jan. 30, 2003

Related U.S. Application Data

(62) Division of application No. 09/205,965, filed on Dec. 4, 1998, now Pat. No. 6,492,809.

(51) Int. Cl.$^7$ .......................... G01V 3/00; G01R 33/20
(52) U.S. Cl. ...................................... 324/303
(58) Field of Search ................... 324/303, 307, 324/309, 314, 306

(56) References Cited

U.S. PATENT DOCUMENTS

| | | | | |
|---|---|---|---|---|
| 4,585,993 A | * | 4/1986 | Bottomley | 324/309 |
| 4,682,106 A | * | 7/1987 | Vatis et al. | 324/307 |
| 4,986,272 A | * | 1/1991 | Riederer et al. | 600/410 |
| 5,023,551 A | * | 6/1991 | Kleinberg et al. | 324/303 |
| 5,245,282 A | * | 9/1993 | Mugler, III et al. | 324/309 |
| 5,280,243 A | * | 1/1994 | Miller | 324/303 |
| 5,447,155 A | | 9/1995 | NessAiver | |
| 5,557,201 A | * | 9/1996 | Kleinberg et al. | 324/303 |
| 5,629,623 A | | 5/1997 | Sezginer et al. | 324/303 |
| 5,705,927 A | * | 1/1998 | Sezginer et al. | 324/303 |
| 5,914,598 A | | 6/1999 | Sezginer et al. | 324/303 |
| 6,051,973 A | * | 4/2000 | Prammer | 324/303 |
| 6,163,153 A | * | 12/2000 | Reiderman et al. | 324/314 |
| 6,232,778 B1 | | 5/2001 | Speier et al. | 324/303 |
| 6,237,404 B1 | | 5/2001 | Crary et al. | 73/152.03 |
| 6,246,236 B1 | | 6/2001 | Poitzsch et al. | 324/303 |
| 6,246,238 B1 | * | 6/2001 | Hennig | 324/307 |
| 6,255,817 B1 | | 7/2001 | Poitzsch et al. | 324/303 |
| 6,291,995 B1 | | 9/2001 | Speier et al. | 324/303 |
| 6,297,632 B1 | | 10/2001 | Speier | 324/303 |
| 6,326,784 B1 | | 12/2001 | Ganesan et al. | 324/303 |
| 6,366,089 B1 | | 4/2002 | Poitzsch et al. | 324/303 |
| 6,373,248 B1 | | 4/2002 | Poitzsch et al. | 324/303 |
| 6,392,410 B2 | | 5/2002 | Luong et al. | 324/303 |
| 6,400,149 B1 | | 6/2002 | Luong et al. | 324/303 |
| 6,492,809 B1 | * | 12/2002 | Speier et al. | 324/303 |
| 6,518,757 B1 | | 2/2003 | Speier | 324/303 |
| 6,518,758 B1 | | 2/2003 | Speier et al. | 324/303 |
| 6,528,995 B1 | | 3/2003 | Speier et al. | 324/303 |
| 6,531,868 B2 | * | 3/2003 | Prammer | 324/303 |
| 6,531,869 B1 | | 3/2003 | Speier et al. | 324/303 |
| 6,538,438 B1 | | 3/2003 | Speier et al. | 324/303 |
| 6,566,874 B1 | | 5/2003 | Speier et al. | 324/303 |
| 6,570,381 B1 | | 5/2003 | Speier et al. | 324/303 |
| 2003/0020473 A1 | * | 1/2003 | Speier et al. | 324/303 |

FOREIGN PATENT DOCUMENTS

WO    WO 98/29639    7/1998

* cited by examiner

*Primary Examiner*—Diego Gutierrez
*Assistant Examiner*—Tiffany A. Fetzner
(74) *Attorney, Agent, or Firm*—Kevin P. McEnaney; Brigitte L. Echols

(57) ABSTRACT

A method and an apparatus for obtaining NMR measurements are disclosed. An NMR measurement apparatus, the measured sample, or both elements may be subjected to motion during the measurement. The envelope of an RF carrier signal is modulated according to an envelope to generate a first sequence of RF pulses. The envelope, the phase of the RF signal, and/or a static magnetic field may be varied during the radiation of the first sequence to substantially saturate a first region of the sample. The first sequence may include additional RF refocusing pulses that, when coupled with movement of the NMR measurement apparatus or sample, may also be used to substantially saturate the first region. A second sequence of RF pulses is radiated to establish a resonance region within the first region and measure an attribute of the sample.

46 Claims, 12 Drawing Sheets

PRECONDITIONING SPINS NEAR A NUCLEAR MAGNETIC RESONANCE REGION IN A BOREHOLE

This is a division of U.S. patent application Ser. No. 09/205,965 filed Dec. 4, 1998, now U.S. Pat. No. 4,492,809.

BACKGROUND

The invention generally relates to preconditioning spins near a nuclear magnetic resonance (NMR) region.

Nuclear magnetic resonance (NMR) may be used to determine properties of a sample, such as body tissue (for medical imaging purposes) or a subterranean formation (for well logging purposes). For example, for the subterranean formation, NMR may be used to determine and map the porosity, formation type, permeability and oil content of the formation.

Referring to FIG. 1, as an example, NMR may be used in a logging-while-drilling (LWD) operation to map the properties of a subterranean formation 10. In this manner, an axisymmetric NMR tool 6 may be part of a drill string 5 that is used to form a borehole 3 in the formation 10. The tool 6 may be, as examples, one of the tools described in Sezginer et. al., U.S. Pat. No. 5,705,927, entitled "Pulsed Nuclear Magnetism Tool For Formation Evaluation While Drilling Including a Shortened or Truncated CPMG Sequence," granted Jan. 6, 1998; Miller, U.S. Pat. No. 5,280,243, entitled "System For Logging a Well During the Drilling Thereof," granted Jan. 18, 1994.

The NMR measuring process is separated by two distinct features from most other downhole formation measurements. First, the NMR signal from the formation comes from a small resonance volume, such as generally thin resonance volume 20a (see FIG. 2), and the resonance volume 20a may have a radial thickness that is proportional to the magnitude of a $\vec{B}_1$ magnetic field (not shown). Depending on the shape of the resonance zones, the volume may extend, as an example, from as little as 1 millimeter (mm) in one direction and as long as several inches in another. Secondly, the NMR measurement may not be instantaneous. Both of these facts combined make the NMR measurements prone to tool motions, such as the NMR tool 6 moving around the periphery of the borehole 3, as further described below.

To perform the NMR measurements, the NMR tool 6 may include permanent magnets to establish a static magnetic field called $\vec{B}_0$ (not shown); a radio frequency (RF) coil, or antenna, to radiate the time varying magnetic field $\vec{B}_1$ that is perpendicular to the $\vec{B}_0$ field; and an RF coil, or antenna, to receive spin-echoes from the formation in response to an NMR measurement, as described below. These two coils may be combined into a single transmit/receive antenna.

As an example, the NMR tool 6 may measure T2 spin-spin relaxation times of hydrogen nuclei of the formation 10 by radiating NMR detection sequences to cause the nuclei to produce spin-echoes. The spin-echoes, in turn, may be analyzed to produce a distribution of T2 times, and the properties of the formation may be obtained from this distribution. For example, one such NMR detection sequence is a Carr-Purcell-Meiboom-Gill (CPMG) sequence 15 that is depicted in FIG. 4. By applying the sequence 15, a distribution of T2 times may be obtained, and this distribution may be used to determine and map the properties of the formation 10.

A technique that uses CPMG sequences 15 to measure the T2 times may include the following steps. In the first step, the NMR tool 6 transmits the $\vec{B}_1$ field for an appropriate time interval to apply a 90° excitation pulse 14a to rotate the spins of hydrogen nuclei (that are initially aligned along the direction of the $\vec{B}_0$ field) by 90°. Although not shown, each pulse is effectively an envelope, or burst, of an RF carrier signal. After the spins are rotated 90° from the direction of the $\vec{B}_0$ field, the spins immediately begin to precess in the plane perpendicular to the $\vec{B}_0$ field at first in unison, then gradually losing synchronization. For step two, at a fixed time T following the NMR pulse 14a, the NMR tool 6 pulses the $\vec{B}_1$ field for a longer period of time (than the NMR pulse 14a) to apply an NMR refocusing pulse 14b to rotate the precessing spins through an additional angle of 180° with its carrier phase shifted by ±90°. The NMR pulse 14b causes the spins to resynchronize and radiate an associated spin-echo 16 (see FIG. 5) which peaks at a time approximately equal to T, after the 180° refocusing NMR pulse 14b. Step two may be repeated "k" times (where "k" is called the number of echoes and may assume a value anywhere from several hundred to as many as several thousand, as an example) at the interval of $t_e$ (approximately 2·T). For step three, after completing the spin-echo sequence, a waiting period (usually called a wait time) is required to allow the spins to return to equilibrium along the $\vec{B}_0$ field before starting the next CPMG sequence 15 to collect another set of spin-echoes. The decay of each set of spin-echoes is observed and used to derive the T2 distribution.

The T2* time characterizes a time for the spins to no longer precess in unison after the application of the 90° excitation pulse 14a. In this manner, at the end of the 90° excitation pulse 14a, all the spins are pointed in a common direction perpendicular to the static $B_0$ field, and the spins precess at a resonance frequency called the Larmor frequency for a perfectly homogenous field. The Larmor frequency may be described by $\vec{\omega}_0 = \gamma \vec{B}_0$, where $\gamma$ is the gyromagnetic ratio, a nuclear constant. However, the $\vec{B}_0$ field typically is not homogenous, and after excitation, the spins de-phase with T2* due to inhomogenieties in the static $\vec{B}_0$ field. This decay is reversible and is reversed by the refocusing pulses 14b that cause the echoes. In addition, irreversible de-phasing occurs (spin-spin relaxation) and is described by the T2 time constant. This results in the decay of successive echo amplitudes in the CPMG sequence according to the T2 time constant. With "inside-out" NMR, typically, spins are measured with T2 >>T2*.

As stated above, the distribution of the T2 times may be used to determine the properties of the formation. For example, referring to FIG. 6, the formation may include small pores that contain bound fluid and large pores that contain free, producible fluid. A T2 separation boundary time (called $T_{CUT-OFF}$ in FIG. 6) may be used to separate the T2 distribution into two parts: one part including times less than the $T_{CUT-OFF}$ time that indicate bound fluids and one part including times greater than the $T_{CUT-OFF}$ time that indicate free, producible fluids.

Each T2 time typically is computed by observing the decay of the spin-echoes 16 that are produced by a particular CPMG sequence 15. Unfortunately, the drill string 5 (see FIG. 1) may experience severe lateral motion. However, the T2 time is approximately proportional to another time constant called a T1 spin-lattice relaxation time. The T1 time characterizes the time for the spins to return to the equilibrium direction along the $\vec{B}_0$ field, and thus, considering both the T1 and T2 times, each spin may be thought of as moving back toward the equilibrium position in a very tight pitch spiral during the T1 recovery. Fortunately, the T1 and T2 times are approximately proportional. As a result, the $T_2$ distribution may be derived from measured T1 times. In fact, the original work on establishing bound fluid cutoffs was done using T1. Those results were then expressed and used commercially in terms of T2. See W. E. Kenyon, J. J. Howard, A. Sezginer, C. Straley, A. Matteson, K. Horkowitz, and R. Ehrlich, *Pore-Size Distribution and NMR in Microporous Cherty Sandstones*, Paper LL (paper presented at the 30th Annual Logging Symposium, SWPLA, Jun. 11-14, 1989).

Polarization-based measurements may use either inversion recovery sequences or saturation recovery sequences. With the saturation recovery sequences, the spin system is saturated, e.g. with several 90° pulses that reduce the magnetization to zero. The spin system is then allowed to recover for a variable length of time prior to applying a monitor pulse or pulse sequence, such as the CPMG sequence. The inversion recovery technique suggests that after the nuclei have aligned themselves along the static magnetic field, a 180° pulse is applied to reverse the direction of the spins. Over time, the spins decay toward their equilibrium direction according to T1, but no measurement is yet made as the 180° pulse does not induce a signal in the detector. Before the decay is complete, however, it is interrupted by a monitor pulse or pulse sequence, such as the CPMG sequence, which rotates the spins into the measurement plane (i.e., induces a signal in the detector). The information of interest is the amplitude of the signal immediately after the initial 90° "readout" pulse. This amplitude clearly depends on the recovery time between the initial 180° pulse and the 90° pulse. Following a determination of amplitude, the spin system is permitted to completely relax back to equilibrium, and the pulse sequence is then repeated.

An example of a downhole use of inversion recovery sequences is described in Kleinberg et. al, U.S. Pat. No. 5,023,551, entitled, "Nuclear Magnetic Resonance Pulse Sequences For Use With Borehole Logging Tools," granted Jun. 11, 1991. However, the inversion recovery sequences described in the '551 patent do not use adiabatic pulses and therefore result in a narrow region of investigation. Also, under "inside-out" conditions in conjunction with motion, it may be easier to saturate a region than to invert it completely. Therefore, saturating a region may be preferred.

Referring back to FIG. 2, the T1 times typically are measured using polarization-based measurements instead of the decay-based measurements described above. In this manner, each polarization-based measurement may first include applying a saturation sequence to saturate the spins in a resonance region (such as the cylindrical resonance volume 20a as depicted in FIG. 2, for example). Subsequently, a polarization period elapses to allow polarization of the resonance volume 20a to the $\vec{B}_0$ static magnetic field. Subsequently, a detection sequence, such as the CPMG sequence, is used to produce spin-echoes from the formation 10. The amplitudes of the first few spin-echoes are then analyzed to determine a polarization weighted integral $\Phi(t_{wait})$ of the porosity distribution $\Phi(T1)$. Because only the first few echoes need to be observed to determine the amplitude of the signal, the T1 measurement may be performed in a shorter duration of time than the decay-based T2 measurement and thus, be less prone to motion of the NMR tool 6. The detection sequence may be successively repeated (after the appropriate saturation sequence) several times with varied wait times to obtain a porosity distribution $\Phi(T1)$.

As an example, a polarization-based measurement may be used to measure the T1 times for hydrogen nuclei in the resonance volume 20a located within the saturated volume 20b (see FIG. 2). In this manner, the NMR tool 6 may first saturate spins within the saturated volume 20b. However, the polarization period may be sufficiently long to permit the NMR tool 6 to significantly move within the borehole. In that case, tool 6 movement causes the resonance volume 20a to shift and causes the NMR tool 6 to receive spin-echoes from a shifted resonance volume 20a' (see FIG. 3) that partially falls outside the original, saturated volume 20b. As a result, the shifted resonance volume 20a' may comprise a region without saturated spins (an effect typically called "moving fresh spins in") and a region of the original saturated volume 20b with saturated spins. Unfortunately, polarization-based NMR techniques may not be able to tolerate "fresh spins" being moved in during the polarization period, as the fresh spins may introduce measurement errors. For example, the measurements may erroneously indicate a higher bound fluid volume than is actually present in the formation.

One way to saturate a larger region is described in PCT Application Ser. No. PCT/US97/23975, entitled "Method For Formation Evaluation While Drilling," filed on Dec. 29, 1997. This application discloses, at the start of a measurement, transmitting one or more radio frequency pulses covering a relatively wide range of frequencies and/or extra wide bandwidth or using one or more pulses which are frequency swept to saturate a cylindrical volume around an NMR tool. The application further describes the use of acceleration peak values to determine when to invalidate measurements due to movement of the tool beyond the extent of the saturated region, the application further describes fitting the tool with stand-offs to prevent movement of the tool beyond the saturated region.

Thus, there is a continuing need for minimizing error introduced by relative motion between an NMR measurement apparatus and a sample being investigated.

SUMMARY

A method for use with an NMR measurement apparatus that is subject to relative motion between the apparatus and a sample is disclosed. The apparatus, the sample, or both elements may be subjected to motion. In one embodiment of the invention, the method comprises radiating a first sequence of RF pulses. The first sequence has an envelope. The envelope is varied during the radiation of the first sequence to substantially saturate a first region of the sample. A second sequence of RF pulses is radiated to establish a resonance region within the first region and measure an attribute of the sample.

In another embodiment, a method for use with an NMR measurement apparatus that is subject to relative motion between the apparatus and a sample comprises using an RF carrier signal to radiate a first sequence of RF pulses. The carrier signal has a phase. The phase is varied during the radiation of the first sequence to substantially saturate a first region of the sample. A second sequence of RF pulses is radiated to establish a resonance region within the first region and measure an attribute of the sample.

In yet another embodiment, an NMR measurement apparatus that is subject to relative motion between the apparatus and a sample comprises at least one magnet to establish a static magnetic field, a first coil, a second coil and an pulse generator. The pulse generator is coupled to the first and second coils and adapted to use the first coil radiate a first sequence of RF pulses to create a time varying magnetic field. The first sequence includes at least one refocusing pulse to produce at least one echo from a resonance region of the sample. The pulse generator is further adapted to use the second coil momentarily modify the static magnetic field at least one time during the radiation of the first sequence to cause saturation of a region larger than the resonance region.

In a further embodiment, a method for use with an NMR measurement apparatus that is subject to relative motion between the apparatus and sample includes using an inversion recovery sequence which comprises at least one or more adiabatic pulses.

Other embodiments of the invention will become apparent from the description, from the drawing and from the claims.

DETAILED DESCRIPTION OF THE PREFERRED EMBODIMENTS

Figure 1:
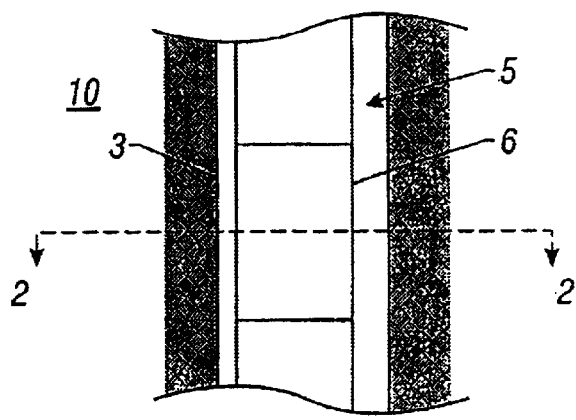
FIG. 1 is a schematic diagram of a subterranean well.
Figure 2:
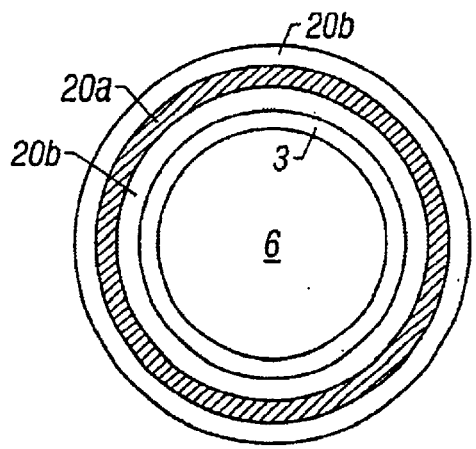
FIG. 2 is a cross-sectional view of the well taken along line 2—2 of FIG. 1.
Figure 3:
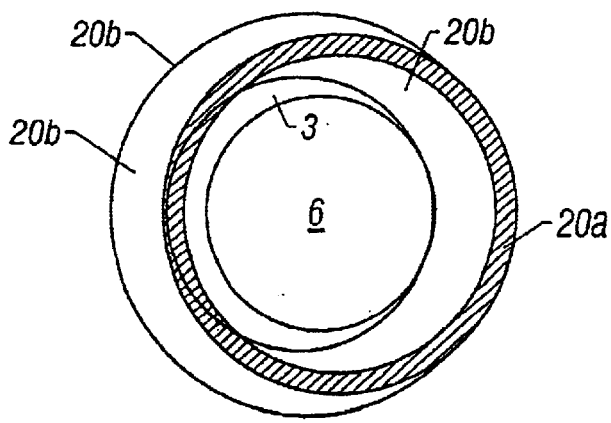
FIG. 3 is another cross-sectional view of the well after movement of the NMR tool.
Figure 4:
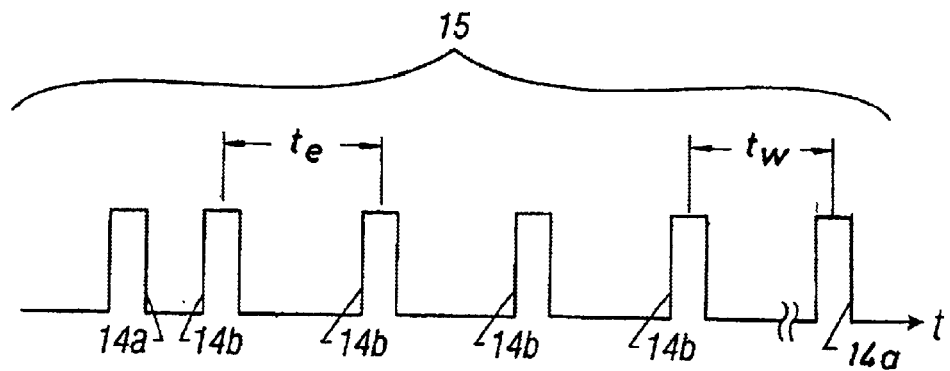
FIGS. 4 and 5 are waveforms illustrating a CPMG pulse sequence.
Figure 5:
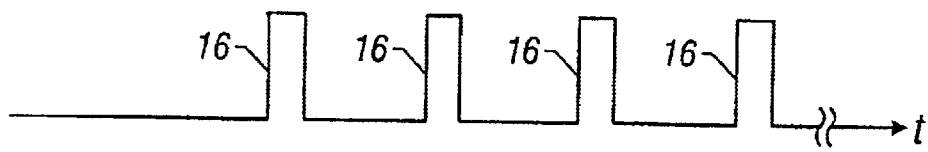
Figure 6:
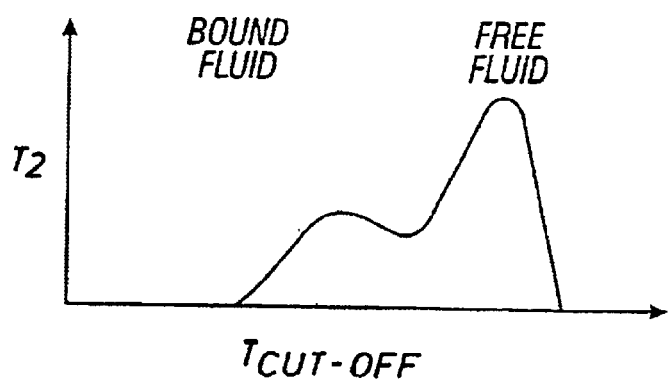
FIG. 6 is an exemplary distribution of T2 relaxation times.
Figure 7:
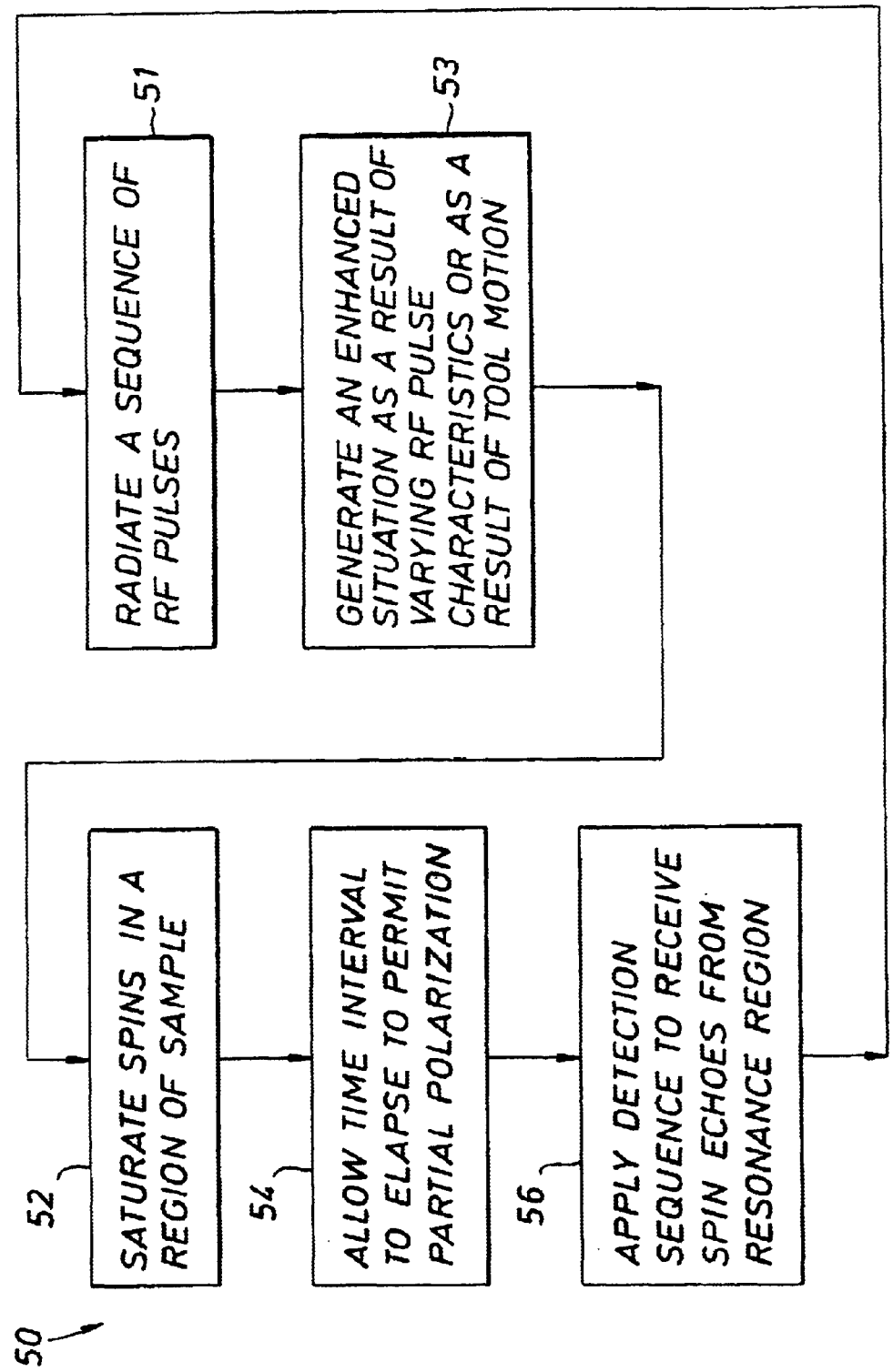
FIG. 7 is a flow diagram illustrating a polarization-based measurement according to an embodiment of the invention.

Referring to FIG. 7, an embodiment 50 of a process to obtain a polarization-based T1 measurement in accordance with the invention may be used by an NMR measurement apparatus (an NMR logging tool, as an example) that is prone to motion. Because the measured sample may be subjected to motion, this process may be used when the sample, the measurement apparatus, or both elements experience motion. The process 50 includes saturating (block 52) spins in a region of a sample whose characteristics are to be measured. Next, a predetermined time interval is allowed to elapse (block 54) to allow at least partial polarization of spins in the region to occur. Subsequently, the process 50 includes applying (block 56) a detection sequence (a CPMG-based sequence, for example) to produce spin-echoes from a resonance region of the sample. As described further below, techniques are used to maximize the boundaries and saturation density of the saturated region to keep the resonance region substantially within the saturated region as the NMR measurement apparatus moves. As a result of these techniques, measurement errors may be reduced and stabilizers for the NMR measurement apparatus may not be needed, for example, if used in a low gradient geometry.

Figure 8:
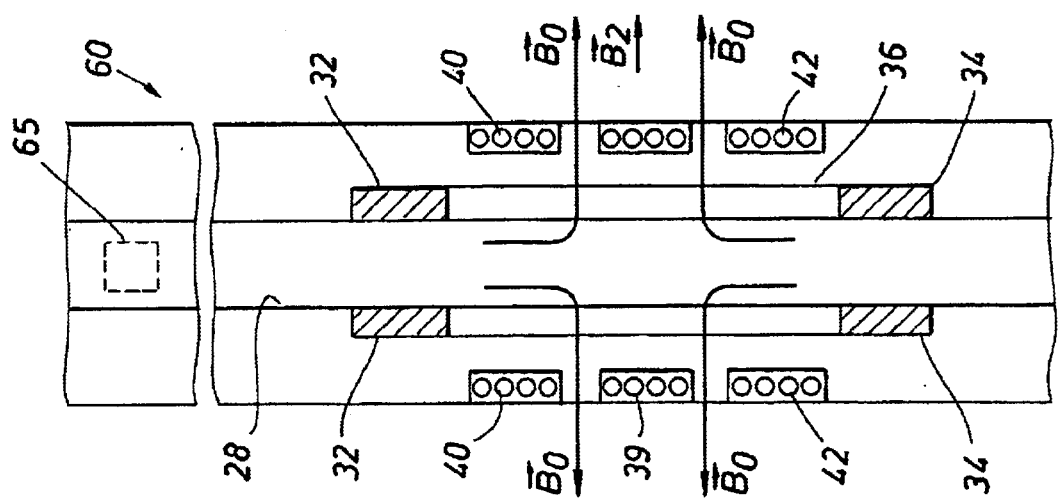

As examples, the process 50, as further described in more detail below, may be used for purposes of mapping the properties of subterranean formations and may also be used in other applications (other "inside out" NMR applications, for example) in which relative motion occurs between a sample and an NMR measurement apparatus. The NMR measurement apparatus, in some embodiments, may include electromagnetic field generating members (a coil, an electromagnet and a permanent magnet, as examples) to generate at least two magnetic fields: a magnetic field called $\vec{B}_0$ (not shown) and a magnetic field called $\vec{B}_1$ (not shown) that is substantially perpendicular to the $\vec{B}_0$ magnetic field. Referring to FIG. 8, as an example, in some embodiments, the NMR measurement apparatus may be an NMR logging while drilling (LWD) tool 60 that includes, as an example, annular permanent magnets 32 and 34 to establish the $\vec{B}_0$ field and a coil 39 to establish the time varying $\vec{B}_1$ field. In some embodiments, the $\vec{B}_1$ field may (when pulsed) have a radio frequency (RF) carrier component called $\vec{\omega}_0$.

The carrier frequency of the $\vec{B}_1$ field may be generally represented by $\omega_0$. The transmission of the $\vec{B}_1$ field creates a resonance region that has a radial thickness, in terms of frequency, that is determined by the gradients of $\omega_0$ and $\omega_1$ in the excited region where $\vec{\omega}_1$ is the projection of $_\gamma \cdot \vec{B}_1$ onto the $\vec{B}_0$ field. In some embodiments, the $\vec{B}_0$ field may also be generated (at least partially) by gradient coils 40 and 42 to cause the $\vec{B}_0$ field to have a component that varies with a low frequency, as described below. The NMR tool 60 may also include processing circuitry may include a pulse generator 65, for example, that is coupled to coil(s) (such as the coils 39, 40 and 42, as examples) and adapted to radiate the $\vec{B}_0$ and/or $\vec{B}_0$ fields in a manner described below.

In principle, each polarization based NMR measurement includes the three building blocks 52, 54 and 56 (see FIG. 7), and one or more measurements may be used to obtain each T1 value. However, the detection sequence (i.e., the block 52) may be used to accomplish the saturation (i.e., perform the functions of block 56) and thus, eliminate the block 52 if two requirements are met: the measurements are successively repeated (called "stacked" experiments), and the signal detection sequence 68 completely destroys the magnetization for the next measurement. If this technique is used, the results from the first measurement are discarded, as the first measurement is performed with an incorrect polarization time. Alternatively, excitation may be performed adiabatically by applying an adiabatic fast passage pulse into the resonance zone just prior to the application of the detection sequence.

Other variations from the three basic blocks 52, 54 and 56 are also possible. As another example, the sequence block 54—block 56—block 52 may also be used to perform each measurement, and this variation may advantageous from a programming point of view. When using the second variation, the first measurement is discarded. Other variations of the process 50 are possible as long as the functions of the block 52, 54 and 56 are achieved.

Another variation of basic blocks 52, 54 and 56 includes blocks 51 and 53. At block 51, radiation of a sequence of RF pulses is initiated. This block 51 may further include the step of identifying a first set of pulse characteristics four the sequence of RF pulses. Next, at block 53, an enhanced saturation region is generated according to a number of different embodiments disclosed herein, The enhanced saturation region may be generated by varying certain or multiple RF pulse characteristics or through the effect of the motion of the NMR tool, both discussed in more detail below. From block 53, control proceeds to the basic blocks 52, 54 and 56, after completion of which, control returns to block 51.

The goal of the saturation, regardless of whether the saturation is being performed by an explicit saturation sequence or by a detection sequence, is to saturate a large region, or volume, with radio frequency (RF) irradiation. As described below in more detail and illustrated by simulations, depending on the particular embodiment, the saturation may be created by applying a sequence of RF pulses, such the CPMG detection sequence, that is tailored to achieve the desired saturation using the motion of the NMR tool 60; by slowly varying a characteristic of the sequence over time with or without motion of the NMR tool 60; by stochastically varying the characteristics of the sequence with or without motion of the NMR tool 60; or by using a combination of these techniques.

A simple CPMG sequence having constant parameters develops sharp saturated regions, called "holes," in the spin distribution. The holeburning is far reaching, but only leads to weak saturation since the holes are well separated from each other. Furthermore, once the magnetization at the positions of the holes is destroyed, continuing the sequence may not increase the saturation further. The motion of the NMR tool 60 may increase the saturation density by "sweeping" these holes over the saturation volume, as described further below.

The CPMG detection sequence may be modified to increase the number of refocusing pulses above the typical number (10, for example) of refocusing pulses that are necessary to measure the initial amplitude of the echo train. This method works well, if motion of the NMR tool 60 during the polarization time is always coupled with motion of the NMR tool 60 during the detection sequence. However, unfortunately, unsatisfactory saturation may occur if the NMR tool 60 is stationary during the detection sequence 68 but moves during the polarization time. Simulations (discussed below) show that this problem may be avoided by slowly changing characteristics of the sequence over time to expand the saturated region, even in the absence of tool motion, as further described below. In this context, the phrase "characteristic of the sequence" may generally refer to an envelope of the sequence or a phase of the RF carrier frequency, as examples. As examples of the possible ways to vary the envelope, the envelope may include pulses 120 (see FIG. 12) that each have a duration (called $t_p$), and the pulses 120 may be spaced apart (from center to center) by time intervals called $t_e$. In this manner, the $t_p$ duration and/or the $t_e$ time interval (as examples) may be varied to expand the saturated region, as further described below.

The characteristics of the detection sequence (i.e., the sequence used for purposes of saturation) may be varied not only slowly but also in an uncorrelated, or stochastic, manner from pulse to pulse, as further described below. The stochastic extremum is the irradiation of incoherent noise. The stochastic variation of the characteristics is to be contrasted to the slow variation of the characteristics in which the saturation affects are far reaching because the coherent, non-stochastic characteristics of the sequence dominate. As a result, slow variation of the characteristics may result in far off resonance holes being incrementally burned by consecutive pulses. The spots where saturation is created during a short time interval are well separated from each other. However, the stochastic variations cause consecutive pulses of the sequence to not contribute to the same hole and saturation creation is spread out more evenly for short time intervals. As a result, the stochastic variation of the pulses generally provides a more consistent saturation density. As described below (and illustrated by simulations), these two techniques may be combined to enhance the performance of the sequence. As also described below, if motion is present that is fast enough to sweep holes over the distance that separates adjacent holes during only a few pulses, the coherent element of the sequences is destroyed, and a sequence with slowly varied characteristics may perform similarly to a sequence with stochastically varied characteristics.

As described below, the flip angles of the refocusing pulses in the CPMG sequence may not need to be large to create off-resonance saturation if coupled with some other variation (variation of the phase of the carrier frequency, for example). Therefore, by shortening the RF pulses, the power necessary for saturation may be decreased. For sufficiently short pulses, the influence of the hole burning is negligible. This being the case, the free evolution period between pulses may be dropped, and saturation may be achieved in much shorter time. In the limit of very short pulses, this technique results in irradiation of incoherent noise whose structure can be designed to fit the needs. In practice, the finite rise and fall times of the pulses set the lower limit of the pulse duration. There may be a tradeoff to be made between time and power necessary to achieve saturation and saturation bandwidth, as described below.

Saturation Using a CPMG Sequence

In the following, an example of saturation using a CPMG sequence with and without slow motion induced changes in $\vec{\omega}_0$ is discussed in detail. Although this description specifically refers to a CPMG sequence, as an example, the above-described hole burning may be accomplished by all multi-pulse sequences that feature a large number of repetitions of a building block of pulses.

The repeated coherent pulsing during a CPMG sequence excites selected spins with $\Delta\omega >> \omega 1$, where $\omega 1$ is approximately equal to the radial thickness of the resonance volume, and $\Delta\omega$ (the distance in frequency space) may be specifically defined by the following equation:

$$\Delta\omega = \gamma \vec{B}_0 - \omega_{rf},$$

where $\omega_{rf}$ is the RF frequency of the $B_1$ field for the first CPMG sequence.

The excitation steps become smaller and smaller with increasing $\Delta\omega$, but the excitations sum up from pulse to pulse, in the holes for significant amounts. Because the transverse magnetization decays in accordance with T2, the selected spins become "saturated." The separation (called $\Delta\omega_h$) of these holes is determined by the periodicity of the sequence. Nonnegligible pulse duration and off resonance effects cause some deviation, so the $\Delta\omega_h$ separation of the holes is approximately described by the following:

$$\Delta\omega_h = \frac{2\pi}{t_c},$$

where $t_e$ is the echo spacing from the beginning of one refocusing pulse to the beginning of the next refocusing pulse.

Coupled with relaxation, the simple CPMG sequence technique results in hole burning at certain off resonance frequencies. It may not be possible to measure in between the burned holes, because the width $\Delta\omega_s$ of the measurement region extends over $\Delta\omega_s \approx 2\omega_1$, which for 180° refocusing pulses of duration $t_p$ becomes $\Delta\omega_{s\approx\pi/tp}$. Since $t_e$ is always greater than $t_p$, $\Delta\omega_s > \Delta\omega_h$ and there may be several holes burned into a resonance region. To calculate the extent of the signal loss, the field geometries, the relaxation times and the detection bandwidth must be taken into account.

Figure 13:
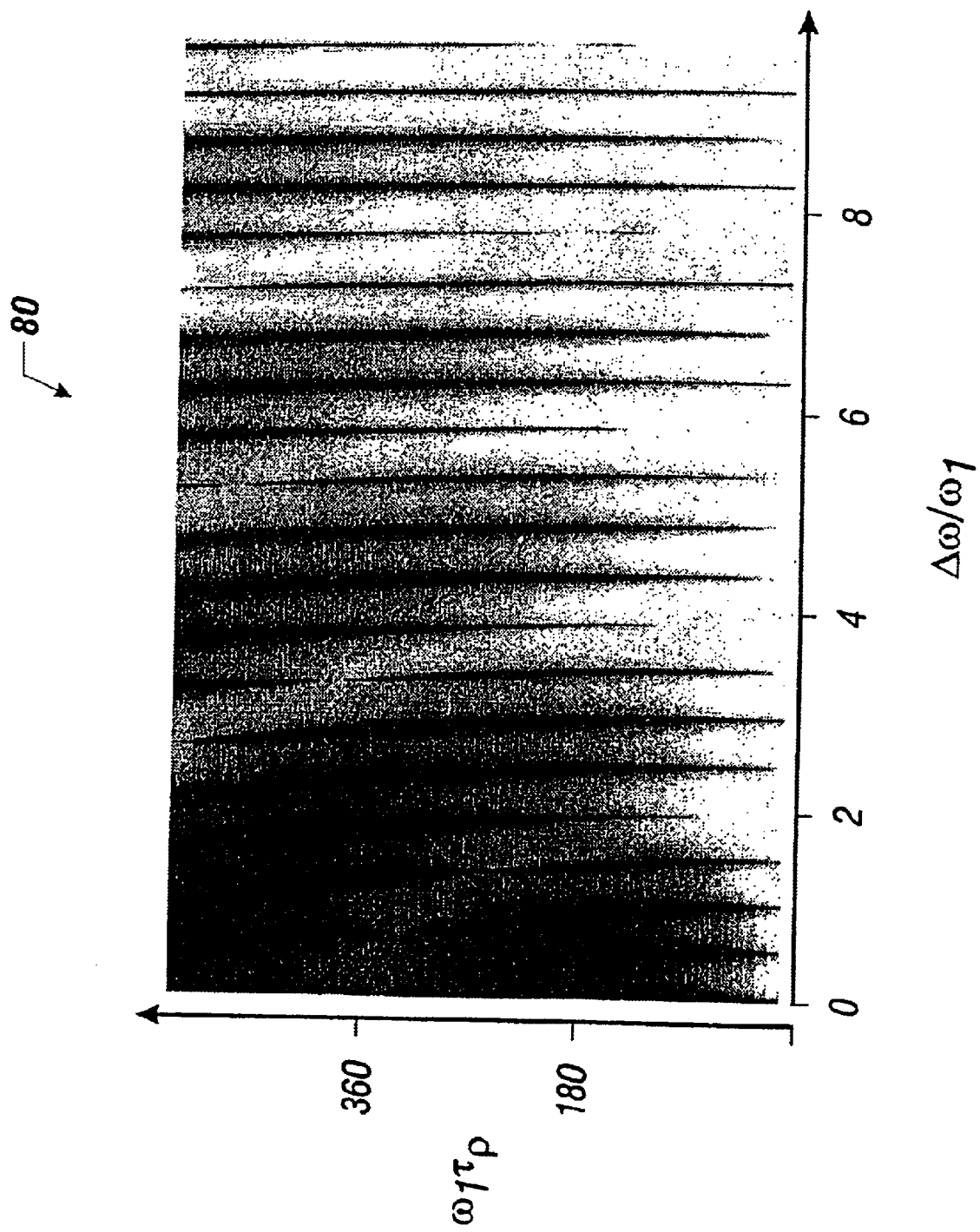
FIGS. 13, 16, 18 and 20 are contour plots showing saturation in a resonance region.

To illustrate the distribution of holes, FIG. 13 is a two-dimensional contour plot 80 (derived from a simulation) showing a calculated contour plot of the distribution of holes burned into a longitudinal magnetization of $M_z$=1 with linear variation in $\omega_0$ on the horizontal axis and $t_p$ on the vertical axis. The white areas represent full conservation of magnetization, and the black areas represent reduction from 100% saturation, or inverted magnetization. The first CPMG sequence is applied at $\Delta\omega$=0 and shown is the effect on the off resonance magnetization $M_z$ immediately after the end of this CPMG sequence. The parameters of the sequence of CPMG pulses are $t_e$=500 $\mu$s, $t_{p180}$=125 $\mu$s, k=1000 where k is the number of refocusing pulses. The relaxation times are chosen to be long, but a fraction of the duration of the echo train. In this simulation, perfectly rectangular pulses were used. However, embodiments of the invention may use substantially rectangular pulses and may use substantially non-rectangular pulses. In FIG. 13, the effect of the first excitation pulse was not simulated.

Figure 14:
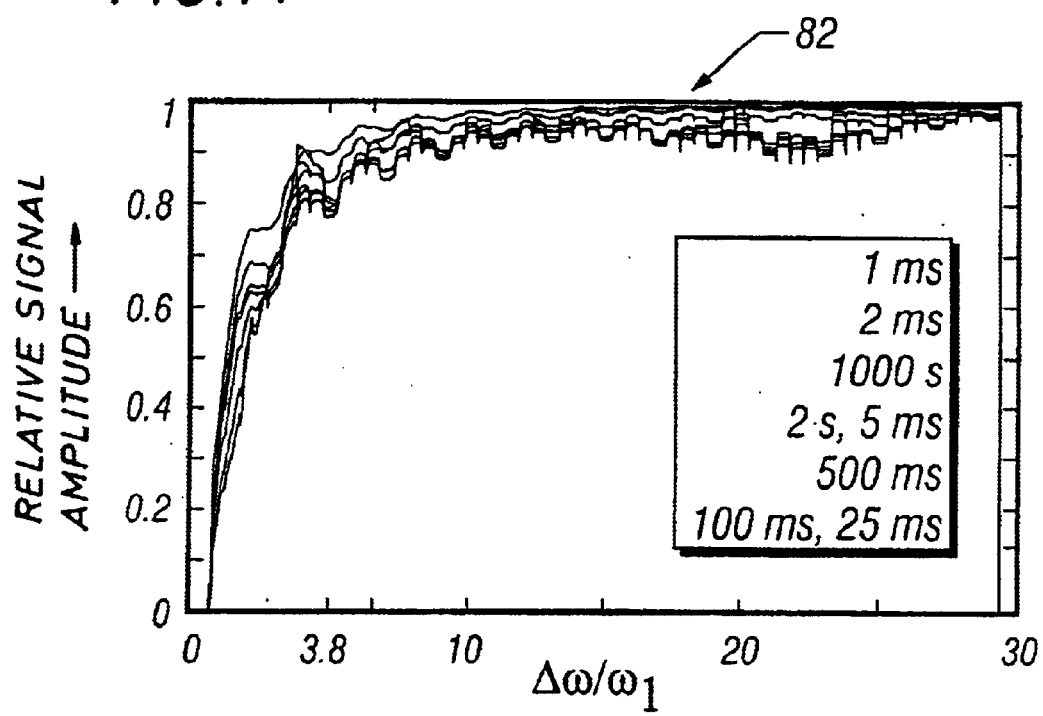
FIGS. 14, 15, 17, 19 and 21 are plots of relative signal amplitudes received from a region surrounding the NMR tool, illustrating saturation.

FIG. 14 shows for several relaxation times, the simulated resultant relative signal amplitudes 82 (i.e., $M_z/M_\infty$) that are available to a second measurement at the frequency shifted by the abscissa $\Delta\omega$, that is reduced by saturation from a first measurement (as described above) for $\omega_1 \cdot t_p = \pi$, when averaging $\Delta\omega = \pm 0.75\omega$. This means that the $\omega_0$ frequency of the carrier has been shifted by $\Delta\omega$ between measurements. The relative signal amplitudes 82 are each associated with a different T1 time (equal to 2*T2, as an example). The parameters for the second measurement were the same as for the first measurement and the flip angle of the pulses was chosen to be 180°. In the figures (and in the simulation), it was assumed that $$\frac{d\omega_1}{d\omega_0} = 0,$$

i.e., the change in the $\vec{B}_1$ field is negligible in the neighborhood of the resonance region. For an axisymmetric gradient geometry, the horizontal scale ($\Delta\omega/\omega_1$) is proportional to the difference in radiuses (of the resonance region) between the first and second measurements. The above assumption that $\omega_1$ is a constant is a valid approximation when the difference in radiuses is much smaller than the radius, a fact that justifies the choice of a constant flipangle in the plot.

Figure 15:
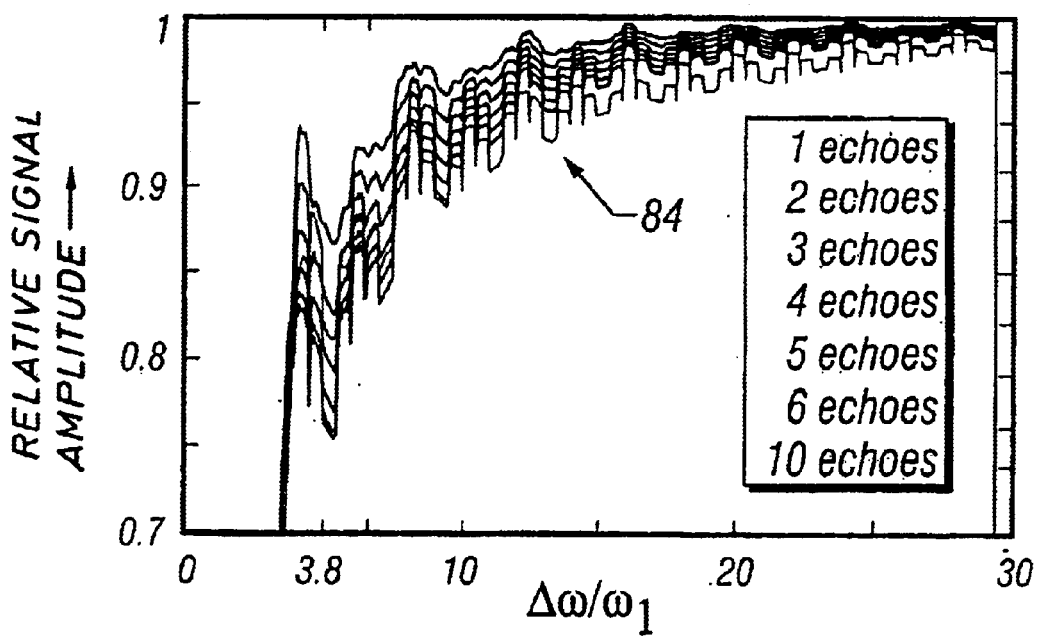

As can be seen from FIG. 14, the saturated region basically extends not further than $2 \cdot \Delta\omega/\omega_1$, that is twice the radial thickness of the resonance region. So, the next measurement starts only with complete saturation, if the resonance region is radially shifted less than $1 \cdot \Delta\omega/\omega_1$. FIG. 15 shows relative signal amplitudes 84 that are each associated with a number of refocusing pulses in the first sequence. As can be seen, most of the saturation at smaller $\Delta\omega$ occurs within the first 10 echoes. Here and in the following examples, T1=2·T2=100 msec was chosen.

Figure 16:
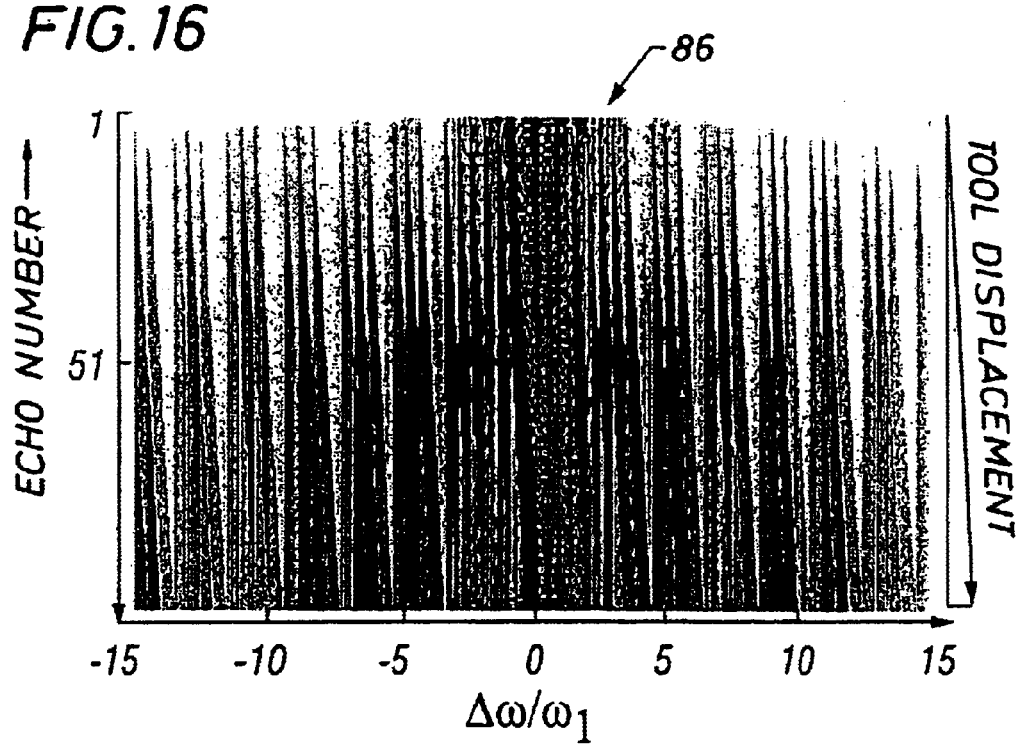

Tool motion during the first CPMG sequence may result in an increased loss in nearby resonance regions. For example, FIG. 16 shows a contour plot 86 of the development of the off resonance $M_z$ magnetization during the first sequence for a translation speed of the tool of $-20\omega_1/s$. The horizontal axis denotes the ratio of off resonance frequency $\Delta\omega_1$ over $\omega_1$ (pulse amplitude) of the first CPMG sequence. The contours describe the relative longitudinal magnetization left after the first CPMG sequence. The amplitude of the pulses are assumed to be constant. The pulse parameters and relaxation times are the same as above. The vertical axis indicates how many refocusing pulses were applied in the first CPMG sequence with carrier $\omega_{RF}$, which is approximately proportional to the duration of this sequence. The number k of refocusing pulses ranges from one refocusing pulse (i.e., a block spanning approximately 500 $\mu$s) for the top plot to 100 refocusing pulses (i.e., a block spanning approximately 50 ms) for the bottom plot. In this example, during 50 ms, the NMR tool 60 travels the distance of +1$\omega_1$, which is roughly half a shell width. In the beginning, carrier $\omega_{RF}$ corresponds to $\Delta\omega$=0, at the end, carrier $\omega$RF corresponds to $\Delta\omega$=+1·$\omega_1$. As shown, with increasing number of echoes, the translation of the NMR tool 60 "sweeps" the holes over the spin distribution and thus, increases the density of the saturation.

Figure 17:
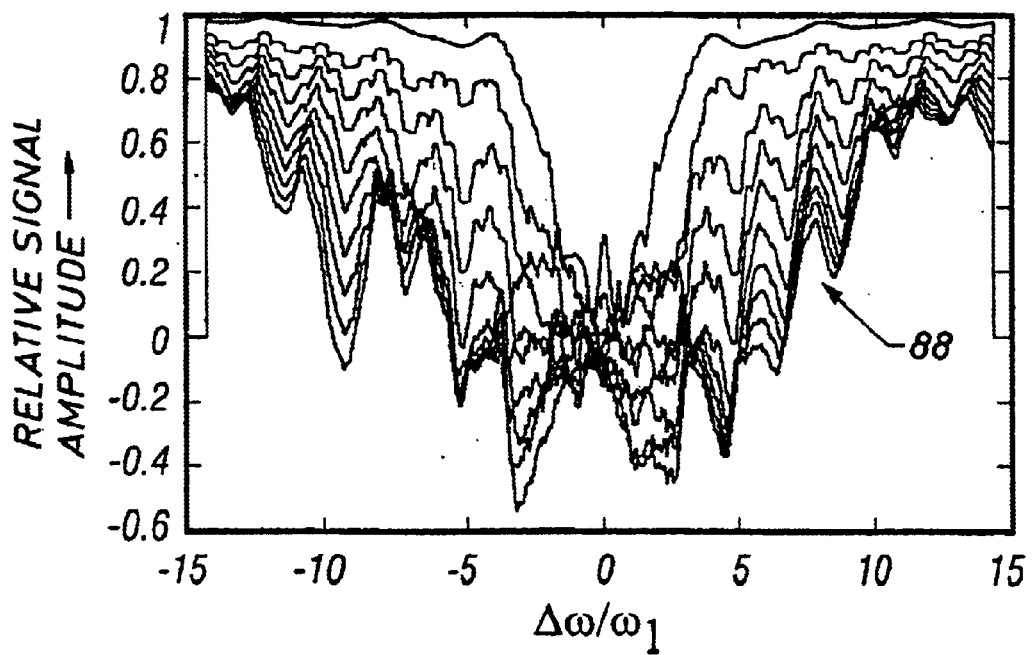

The resulting relative signal amplitudes (i.e., $M_z/M_\infty$) 88, when averaging over a (rectangular, for purposes of the simulation) shell of width $\pm 0.75\omega_1$ is shown in FIG. 17. From top to bottom, the amplitudes 88 represent the result for k=1, 11, 21, 31, 41, 51, 61, 71, 81, 91. Note that the loss increases with echo number and for more than 10 echoes becomes much stronger than the saturation effect without motion of the NMR tool 60, as shown in FIGS. 14 and 17. The saturated region has now a width of more than 5·$\omega_1$. The loss increases for a time comparable to the relaxation times of the spin and can even lead to negative signal for small $\Delta\omega$. The exact profile depends on the motion and on the relaxation times of the spin ensemble. The profile gets narrower for smaller relaxation times.

It is assumed above that the pulses in the CPMG sequences are perfectly rectangular pulses. However, real "rectangular" pulses may never reach this ideal but may be subject to finite rise and fall times. This limits the width of the frequency spectrum contained in the pulses. At far off resonance, the width of the burned holes and the speed of burning them becomes proportional to the amplitude of the frequency component of the pulse at the position of the hole. Therefore, in some embodiments, far off resonance hole burning may be less effective than in the simulations described above.

For the pulses discussed in this application, a wide frequency distribution is beneficial. Therefore, in some embodiments, rectangular pulses with the shortest possible rise and decay time constants may be preferred. Furthermore, the saturation region can be optimized by varying the shape of the pulse envelope to adapt the frequency content of the pulse.

In general, far reaching saturation in the absence of motion may be created by irradiating a repetitive multipulse sequence with varying parameters and broad band pulses. If the pulse sequence parameters are slowly varied while the sequence is applied, the positions of the burned holes move slowly over the spin distribution and increase the saturation. Varied pulse sequence parameters include:

variation of the pulse separation, $t_e$, variations of $t_p$, variations of $\vec{\omega}_1$ by, as examples, pulse amplitude, field direction and carrier frequency, $\omega_{RF}$, variation of $\vec{\omega}_0$, and variation of the pulse phase.

Variations of combinations of these parameters and variations of other parameters are also possible. Variations in $\vec{\omega}_0$ and $\vec{\omega}_1$ may be caused by actual variations of the $\vec{B}_0$ and $\vec{B}_1$ fields (e.g., variation of magnet and antenna spacings or orientations and/or rf power) or by relative motion of sample and the NMR tool 60. In this manner, relative motion of the sample with respect to the NMR tool 60 may stem from motion of the sample (e.g., fluid flow or diffusion) or from tool motion.

Another way to vary $\vec{\omega}_0$ is to vary the static field with the help of an electromagnet, or "gradient coil." For example, referring back to FIG. 8, in some embodiments, the NMR tool 60 may include the upper 32 and lower 34 permanent magnets that circumscribe a sleeve 28 of the NMR tool 60 and produce a radial, axisymmetric $\vec{B}_0$ field. The magnets 32 and 34 are polarized in a direction parallel to the longitudinal axis of the NMR tool 35 to cooperate with each other to provide a low gradient $\vec{B}_0$ field. As an example, the north poles of the magnets 32 and 34 may face each other to furnish a $\vec{B}_0$ field having field lines that extend radially away from the longitudinal axis of the NMR tool 60. In some embodiments, a magnetically permeable member 36 may circumscribe the sleeve 28 and may be positioned between the upper 32 and lower 34 magnets. As a result of this arrangement, the magnetically permeable member 36 focuses the $\vec{B}_0$ field to minimize the gradient of the $\vec{B}_0$ field, and thus, produce a more uniform $\vec{B}_0$ field in the region of interest. The NMR tool 60 may or may not include the sleeve 36. More detailed descriptions of these arrangements may be found in U.S. patent application Ser. No. 09,033,965, entitled "Nuclear Magnetic Resonance Apparatus and Method For Generating an Axisymmetric Magnetic Field Having Straight Contour Lines in the Resonance Region," filed on Mar. 3, 1998; and U.S. Pat. No. 4,350,955, entitled "Magnetic Resonance Apparatus," granted Sep. 21, 1982, both of which are hereby incorporated by reference.

To vary the $\vec{B}_0$ field, NMR tool 35 may include gradient coils, such as coils 40 and 42, that also circumscribe the sleeve 28. The coils 40 and 42 may be pulsed with a DC current (by a pulse generator, such as the pulse generator 65) to produce an additional component, $\vec{B}_2$, to the $\vec{B}_0$ field. $\vec{B}_2$ is substantially radial if the currents in coils 40 and 42 flow in opposite directions. The coils 40 and 42 may be positioned between the magnets 32 and 34 so that both coils 40 and 42 contribute a positive component to the $\vec{B}_0$ field that may or may not be substantially aligned with the $\vec{B}_0$ field in the region of interest, depending on the embodiment. In some embodiments, the coils 40 and 42 may be formed either from a pair of single or multi-turn current loops with currents equal in magnitude and opposite in direction of circulation. For example, the coils 40 and 42 may form a saddle coil.

Figure 9:
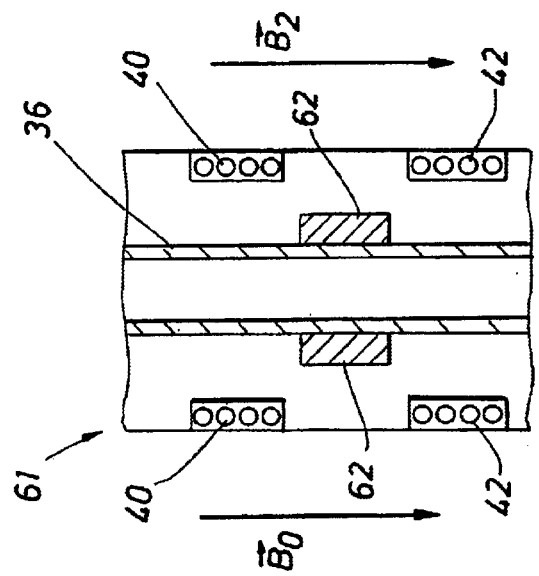
FIGS. 8, 9 and 10 are schematic diagrams of NMR tools according to different embodiments of the invention.

Other embodiments that use the gradient coils 40 and 42 in conjunction with a radial, axisymmetric $\vec{B}_0$ design are possible. For example, referring to FIG. 9, in another NMR tool 61, the permanent magnets 32 and 34 may be replaced by an annular permanent magnet 62 that circumscribes the sleeve 36, for example, and is located between the coils 40 and 42. The magnet 62 produces $\vec{B}_0$ field lines that extend axially parallel to the axis of the tool 61. To make $\vec{B}_2$ substantially parallel to $\vec{B}_0$, the currents in coils 40 and 42 must flow in the same direction. As an example, the top of the magnet 62 may form the north pole of the magnet 62, and the bottom of the magnet 62 may form the south pole.

Figure 10:
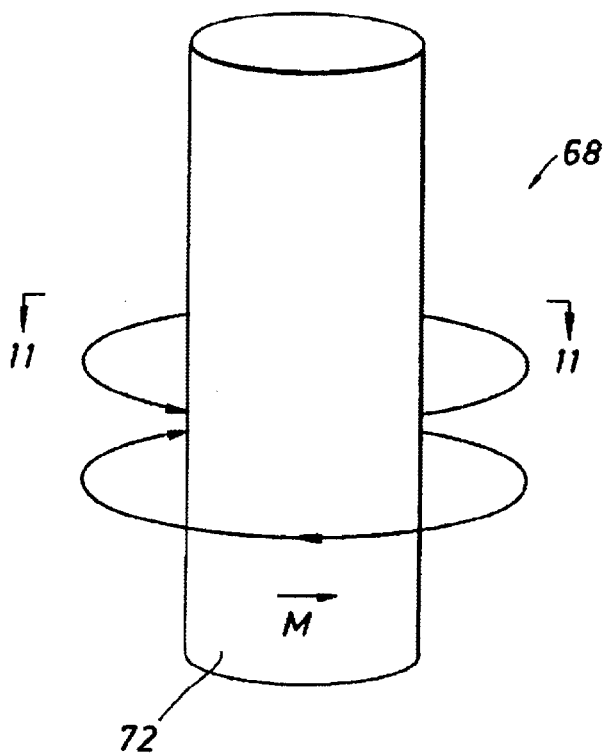
Figure 11:
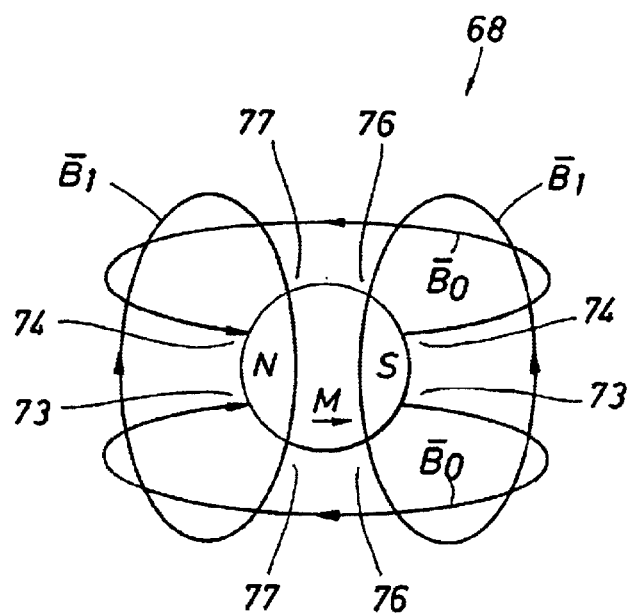
FIG. 11 is a cross-sectional view of an NMR tool taken along line 11—11 of FIG. 10.

Arrangements other than the radial, axisymmetric $\vec{B}_0$ designs described above are also possible. For example, gradient coils may be used with two-dimensional (2-D) dipolar $\vec{B}_0$ designs. An example of a 2-D dipolar $\vec{B}_0$ design may be found in U.S. Pat. No. 5,280,243, entitled "System For Logging a Well During the Drilling Thereof," granted Jan. 18, 1994, issued to Melvin Miller. In this manner, an NMR tool 68 that uses a 2-D dipolar $\vec{B}_0$ design may include an annular magnet 72 that establishes a dipole pattern for the $\vec{B}_0$ field as shown in FIGS. 10 and 11. Unlike their counterparts in the tools 60 and 61, RF coils 73 and 74 are not concentric with the longitudinal axis of the tool 68, but rather, the RF coils 73 and 74 are arranged to produce a dipole pattern in the $\vec{B}_1$ field so that the contour lines of the $\vec{B}_1$ field are substantially perpendicular to the contour lines of the $\vec{B}_0$ field in the resonance region. The tool 68 may include gradient coils 76 and 77 that each may include one or more rectangular loops to produce a gradient field that are aligned with the $\vec{B}_0$ field in the region of interest that is established by the magnet 72.

Thus, as a result of the above-described arrangements, the spins precess around $\vec{\omega}_0 + \vec{\omega}_0^{gradient}$. The largest effect occurs if both vectors are parallel. Thus, as a result of this technique, $\Delta\omega$ may be varied without varying $\omega_{rf}$. This is advantageous to varying $\omega_{rf}$ because the bandwidth of an antenna with high quality factor limits the range of possible variation for $\omega_{rf}$ (without retuning the antenna, which is impractical during a saturation sequence at least if it is done by switching capacitors using mechanical switches). In some embodiments, a drawback of this method may be the relatively large amount of energy needed for driving the electromagnet (compared to the use as an imaging device) if it must be fired with varying amplitudes throughout the saturation sequence. There are several ways to use the gradient coil (or coils):

Substantially constant current is established in the gradient coil throughout one pulse (of the $\vec{B}_1$ field) to effectively shift the radius of the resonance region for this pulse.

The current in the gradient coil is varied throughout one pulse (of the $\vec{B}_1$ field) to create a "sweep" pulse without varying the frequency of the rf pulse. Depending on the actual parameters, the sweep pulse may invert, excite or saturate a particular region. This technique may be used in an inversion recovery sequence (instead of a saturation sequence) to invert a large region around the NMR tool.

The gradient coil is fired between the pulses (of the $\vec{B}_1$ field) to destroy possibly conserved transverse magnetization. If the gradient pulse duration (called $t_{grad}$) is so short that the variation of $\alpha = \vec{\omega}_0^{gradient} t_{grad}$ over the saturated region is negligible this is similar to stochastically varying the phase of the pulses of the $\vec{B}_1$ field.

The current in the gradient coil may be pulsed concurrently with each pulse of the $\vec{B}_1$ field.

The gradient coil may be used to create the stochastic or continuous variations described above.

Other uses of the gradient coil are possible.

CPMG Sequence with Stochastic Variations

Figure 18:
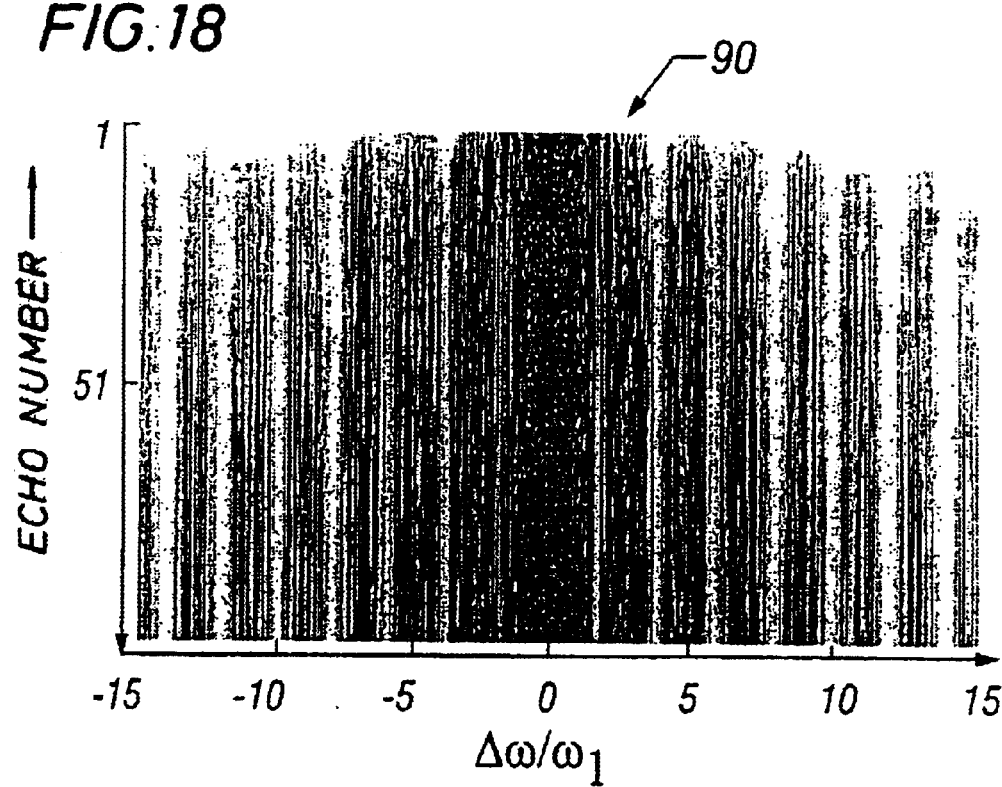
Figure 19:
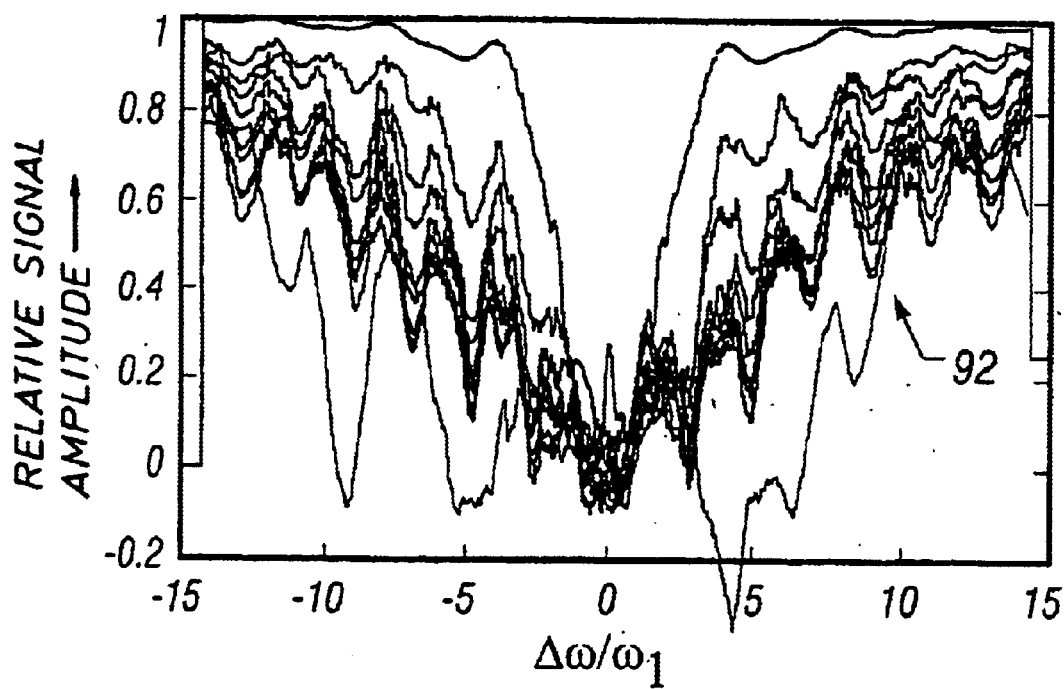

The pulse train characteristics of the CPMG sequence may also be stochastically varied. For example, the phase of the RF carrier pulse may be randomly varied to randomly to create 0°, 90°, 180° and 270° pulse phases (at least these pulse phases are available in typical NMR spectrometers), as examples. Referring to FIG. 18 (showing a contour plot 90 of relative signal losses for different echo numbers) and FIG. 19 (showing a contour plot 92 of relative signal losses for different echo numbers when averaged over a volume thickness of $\pm 0.75_{\omega 1}$), an example is shown where the pulses are randomly generated, and the tool 60, 35 does not move. Except for this randomization of the pulse phases, all spin and pulse parameters are the same as in the examples described above.

As can be seen, the saturation burns wide and well-separated stripes into the spin distribution. The width of the saturated region is smaller than the width of the region created by the motion influenced CPMG sequence, but the saturation profile is much smoother than the one created with a CPMG sequence. This indicates a tradeoff between the extent of the resonance region (using coherent features) and reliable quantitative saturation profile (using stochastic features). It should be noted that the profiles created by a CPMG sequence will provide a smoother shape too for spins with $T_{1,2}$ (here 100 ms) $<< t_m$ (here 50 ms), where $t_m$ is the duration of the CPMG sequence. The occurrence of motion during application of the random phase sequence slightly increases its performance, but the profile stays smooth.

Figure 20:
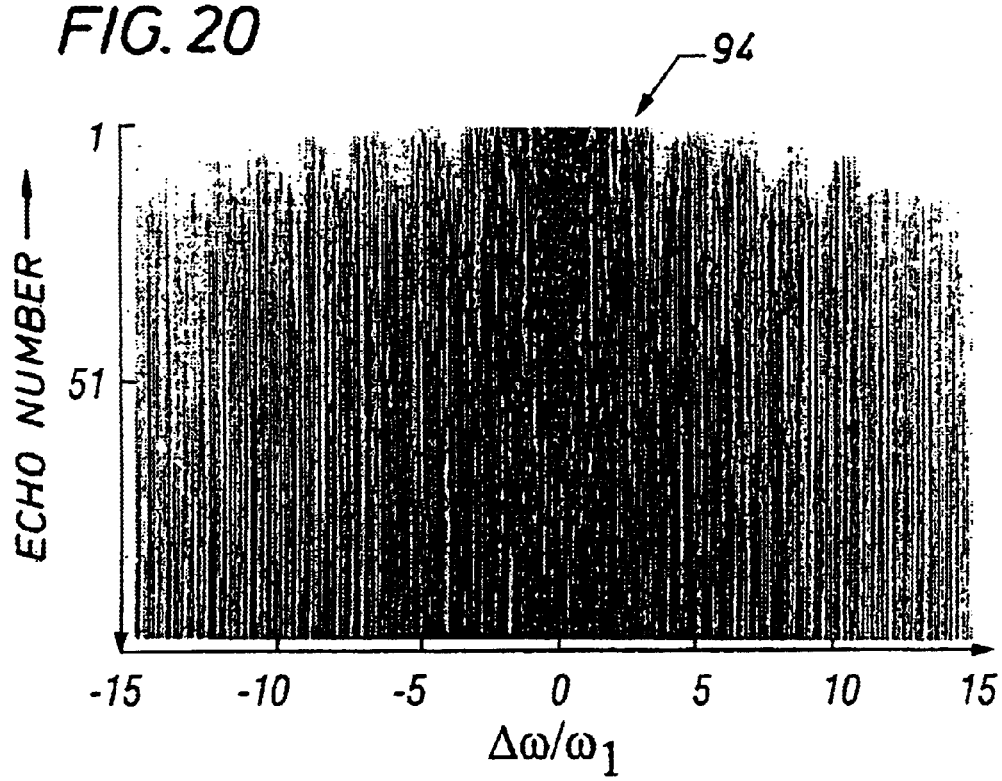

The stripes of incomplete saturation occur because not every hole is burned with the same "speed." Depending on the position $\Delta\omega$, some holes may even be completely suppressed as can be seen, as an example, in FIG. 20 where every fourth hole is missing. The position of these insufficiently saturated spots depends on the duration of the refocusing pulse: Off resonance, a pulse of duration $t_p$ rotates a spin through the angle $\alpha(\Delta\omega) = \sqrt{\omega_1^2 + \omega^2} t_p$ around its "effective rotation axis" that points in the direction $\vec{\omega}_1 + \vec{\Delta}\omega$. The unsaturated "nodes" appear where $\alpha$ is a multiple of $2_{90}$. Therefore, by varying $\omega_1 \cdot t_p$, these spots may also be saturated.

Figure 12:
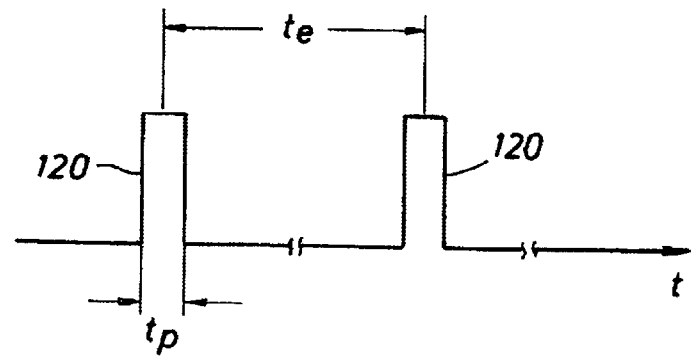
FIG. 12 is a waveform illustrating an NMR pulse sequence.
Figure 21:
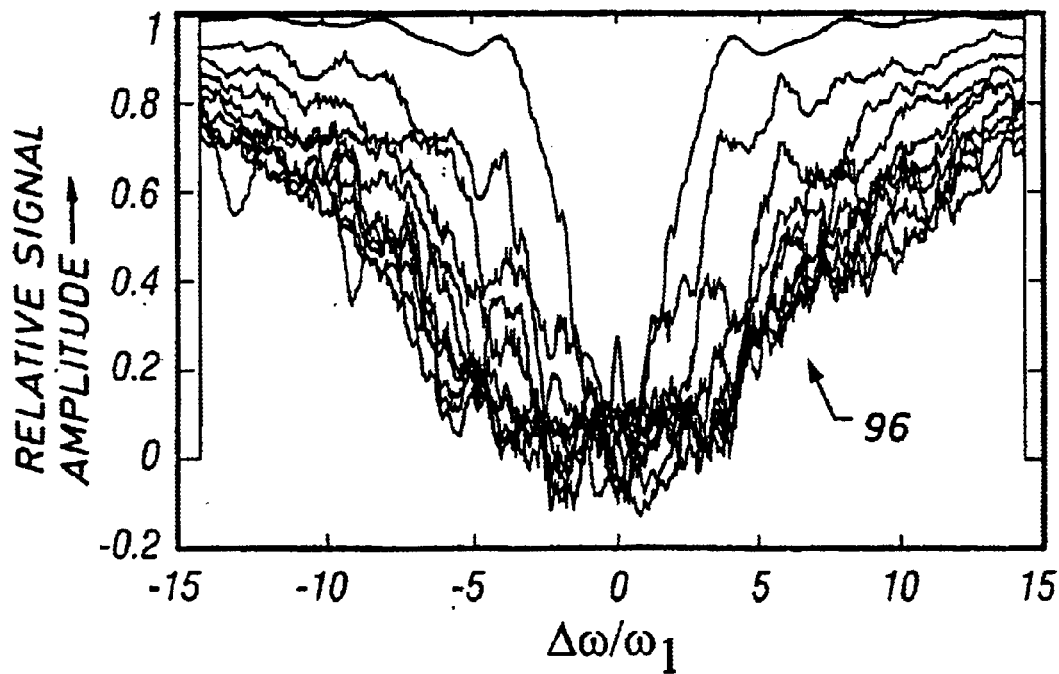

This effect is illustrated in FIG. 20 (showing a contour plot 94 of relative signal losses for different echo numbers) and FIG. 21 (showing plots 96 of relative signal losses for different echo numbers when averaged over a radial volume thickness of $\pm 0.75\omega_1$) for the example of slowly increasing pulse length (denoted "$t_p$" in FIG. 12). In this simulation, the pulse length was increased linearly from 125 µs (a 180° pulse) for the first refocusing pulse to 250 µs is (a 360° pulse) for the 100th refocusing pulse while $t_{free}$ (the distance between pulses, as depicted in FIG. 12) was kept fixed. All other parameters are the same as in the previous example. The resulting saturation profile is smoother and slightly wider than without variation of the pulse length.

Again, in general the saturation effect of the pulse sequence may be optimized for a particular range of motion by varying the various parameters of the sequence, like $t_e$, which is about inversely proportional to the separation of the burned holes, $t_p$, the pulse phases, etc. and trading off between coherent and stochastic features.

The previous examples of saturation sequences used the far-off-resonance hole burning effect to create saturation. As stated above a pulse of duration $t_p$ rotates a spin that is off resonance through the angle $\alpha(\Delta\omega)$ which is always bigger than the nominal flip angle $\alpha(0)$. Therefore for refocusing pulses with $\alpha(0) = 180°$ (i.e., "180 degree pulses"), it always holds $\alpha(\Delta\omega) > 180°$ for off resonance. On the other hand, optimal excitation and thus, optimal excitation off resonance occurs if $\alpha(\Delta\omega) = (2n+1) \cdot 180°$. Then the effective flip angle through which a spin is turned away from the longitudinal axis is $\theta = \theta_{max}$ with $\theta_{max} = \alpha(\Delta\omega) = 2$ arctan $$\theta_{max} = \alpha(\Delta\omega) = 2\arctan\left(\frac{\omega_1}{\Delta\omega}\right)$$

being the maximum effective flip angle for a given $\Delta\omega$. Therefore using 180° pulses to create off resonance saturation may waste energy.

Figures 22, 23:
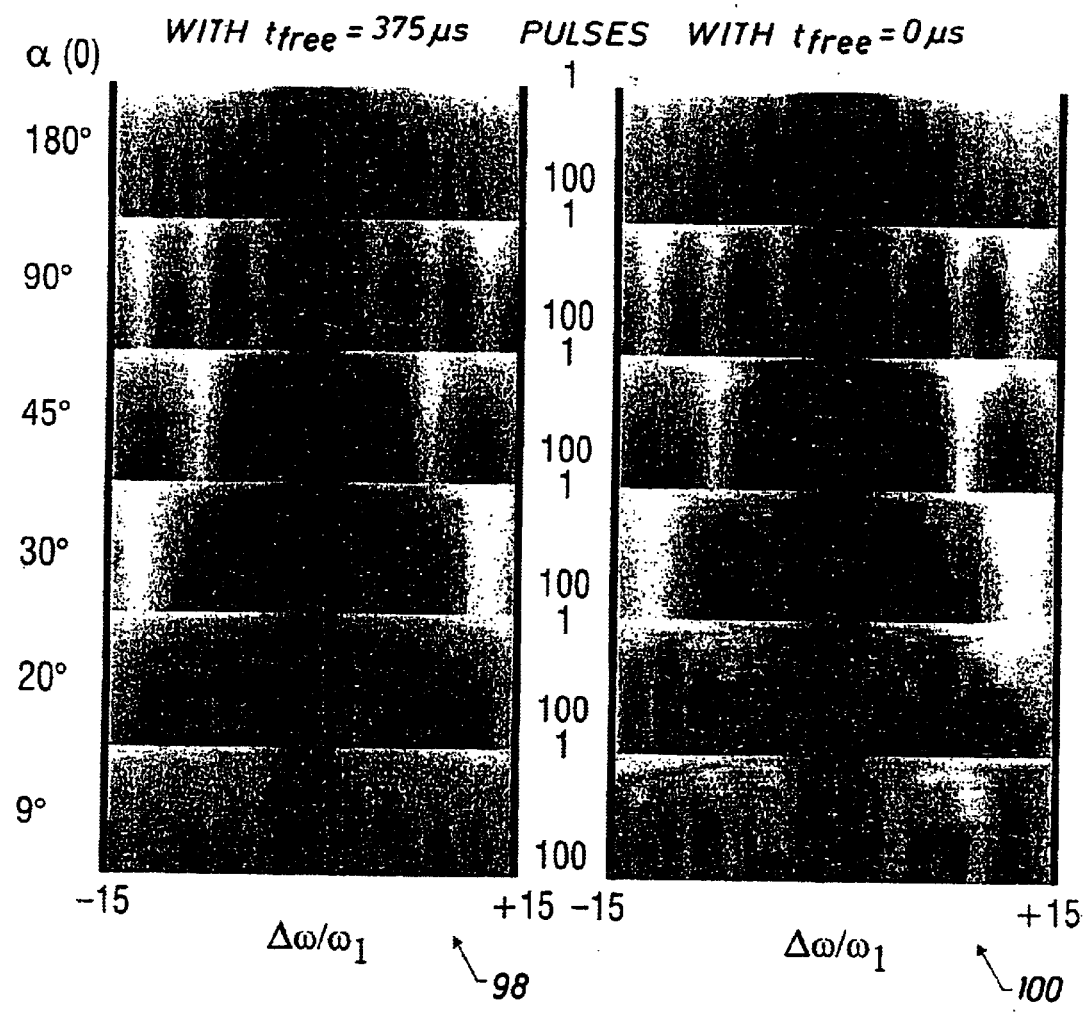
FIGS. 22 and 23 are contour plots illustrating saturation in a resonance region for different numbers of pulses with and without interleaved free evolution periods.

FIGS. 22 and 23 illustrate the dependence of the saturation profile (averaged over a resonance shell thickness) on $\alpha(0)$ of the refocusing pulses used in the sequence. The phases are varied stochastically as previously described. In FIG. 22, relative signal losses 98 are illustrated for the $t_{free}$ free evolution time (i.e., the time interval between refocusing pulses, as illustrated in FIG. 12) being set to 375 µs, and in FIG. 23, relative signal losses 100 are illustrated for the $t_{free}$ time being set to zero. In both FIGS. 22 and 23, the signal losses 98 and 100 are illustrated for 1 to 100 pulses for the flip angles 9°, 20°, 30°, 45°, 90° and 180° as a function of $\Delta\omega$. The different flip angles are created by varying the $t_p$ pulse duration. As can be seen, the signal loss distributions are almost identical for different $t_{free}$ times, and thus, under stochastic phase variation, the saturation pattern is determined mainly by the pulse duration and not by the duration of the free evolution period.

The minimal pulse duration that can be used with a given hardware is determined by the rising time constant (called $t_r$) of the pulse. If $t_p < 3t_r$, then the pulse does not reach the maximum $\omega_1$ before it is switched off and it rapidly becomes less effective when $t_p$ is reduced further. For a well logging NMR apparatus a good estimate is $t_r = 5 \ldots 30$ µs.

When $t_p$ decreases, the saturated region becomes broader. Of practical interest is mainly the region with $|\Delta\omega| <$ $$|\Delta\omega| < \sqrt{\left(\frac{2\pi}{t_p}\right)^2 - \omega_1^2},$$

that is, the region with $\alpha(\Delta\omega) < 2_\pi$ within the two inner unsaturated nodes. The maximum flip angle $\theta_{max}$ decreases with increasing $\Delta\omega$. Therefore, the wider the saturation region, the more pulses are needed to create saturation in the outer parts of the region. If the time constant for saturation is $T_s$, then only spins with $T_1 > T_s$ can be saturated fully. Therefore, a tradeoff may be made between saturation bandwidth and lowest $T_1$ that still can be saturated. Also this shows that, in some embodiments, it is advantageous to keep the sequence as short as possible by minimizing $t_{free}$ to the lowest possible value that can be obtained with the available hardware (the hardware problems here may include phase switching time, pulse rising and falling times and overloading the RF circuitry with long continuous rf pulses).

Figures 24, 25:
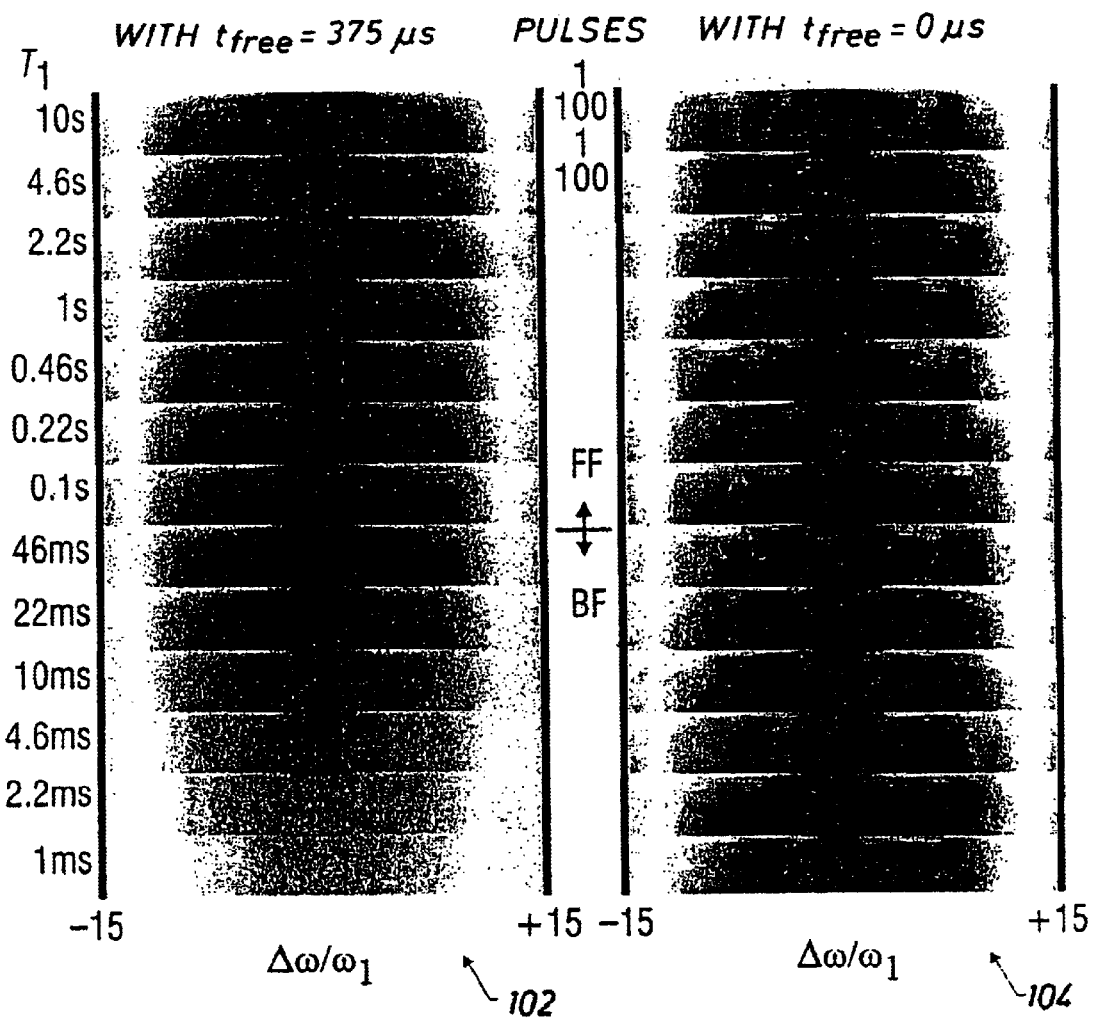
FIGS. 24 and 25 are contour plots illustrating saturation in a resonance region for different numbers of pulses with and without interleaved free evolution periods.

FIGS. 24 and 25 illustrate the losses 102 and 104 for sequences with (FIG. 24) and without (FIG. 25), $t_{free}$, respectively. The losses 102 and 104 are shown for different relaxation times. With $t_{free}=375$ μs, the sequence of 100 refocusing pulses is 40 ms long, and without the free evolution period, the sequence is only 2.4 ms long. For a nominal flip angle $\alpha(0)=35°$, both sequences are capable of saturating spins with relaxation times of free fluid (T1>50 ms), but the sequence without free evolution period is capable of saturating spins with 20 times lower $T_1$ which is needed if one wants to resolve spin distributions within the bound fluid. In both cases, the energy needed to create the saturation is 100

$$100 \cdot \frac{35}{180} \approx 20$$

times the energy for a single 180° refocusing pulse which should pose no serious problem for downhole NMR spectrometers which usually are able to create trains of hundreds of 180° refocusing pulses out of energy stored in capacitors during $t_W$.

In some embodiments, the profiles burned with sequences that include a free evolution period are somewhat smoother than the patterns burned by continuous irradiation. This might stem from additional dephasing that occurs during the free evolution period that is missing in the second case, but is not critical. In addition, if a tool with axisymmetric field geometries is displaced by the distance $\vec{\Delta r}$, every spin, depending on its position on the azimuth, experiences a different displacement in frequency space $\Delta\omega = d\omega_0/d\vec{r} \cdot \vec{\Delta r}$. This leads to an additional effective smoothing of the actual saturation profile.

In the simulations the four pulse phases were chosen using a random generator. Therefore the performance of a sequence varied slightly from simulation to simulation. In some embodiments, a predetermined sequence of phases might be used to optimize the saturation performance. In some embodiments, an optimal parameter variation may be one without periodicity.

In summary, exemplary techniques for preconditioning spins in the neighborhood of the NMR resonance region are described above. These techniques permit polarization-based T1 measurements even if the NMR measurement apparatus (the NMR tool 60 or 35, as examples) is moving with respect to the sample, and these techniques permit polarization based measurement while drilling unstablized, at least together with a low gradient as described in U.S. patent application Ser. No. 09,033,965, cited above. To be able to operate without a stabilizer makes the tool more "driller friendly," and therefore greatly increases the usability of a logging while drilling (LWD) tool.

While the invention has been disclosed with respect to a limited number of embodiments, those skilled in the art, having the benefit of this disclosure will appreciate numerous modifications and variations therefrom. It is intended that the appended claims cover all such modifications and variations as fall within the true spirit and scope of the invention.

What is claimed is:

1. A method for use with an NMR measurement apparatus located in a borehole surrounding an earth formation and subject to relative motion between the apparatus and a sample located in an investigation region of the earth formation, the method comprising:

selecting a set of initial RF pulse characteristics defining one or more RF pulses;

radiating a first sequence of RF pulses to substantially saturate a first region of the sample, the first sequence comprising two or more RF pulses and having an envelope, the envelope defined by RF pulse characteristics associated with individual RF pulses, the RF pulse characteristics selected from the group including, amplitude, phase, duration and time interval between RF pulses;

varying at least one of the group of RF pulse characteristics of the envelope for one or more subsequent RF pulses within the first sequence during the radiation of the first sequence to substantially saturate the first region of the sample;

radiating a second sequence of RF pulses to establish a resonance region within the first region;

detecting an NMR response to the second sequence from the resonance region within the first region; and measuring an attribute of the sample of the earth formation based on the NMR response.

2. The method of claim 1, wherein the act of varying the RF pulse characteristic comprises:

varying durations of the RF pulses in the first sequence to vary spin flip angles during the first sequence.

3. The method of claim 1, wherein the act of varying the RF pulse characteristic comprises:

varying the envelope of the first sequence of RF pulses in an uncorrelated manner.

4. The method of claim 1, wherein the act of varying the RF pulse characteristic comprises:

slowly varying the envelope with respect to durations of RF pulses of the first sequence.

5. The method of claim 1, wherein the first region is large enough to accommodate the relative motion between the apparatus and the sample.

6. The method of claim 1, wherein the act of varying the RF pulse characteristic comprises:

varying amplitudes of the RF pulses in the first sequence.

7. The method of claim 1, wherein the act of varying the RF pulse characteristic comprises:

varying spacings between the RF pulses in the first sequence.

8. The method of claim 1, wherein the act of varying the RF pulse characteristic comprises:

varying durations of the RF pulses in the first sequence.

9. The method of claim 1, wherein the relative motions occurs due to movement of the NMR apparatus.

10. The method of claim 1, wherein the NMR measurement apparatus comprises a logging while drilling tool.

11. The method of claim 1, wherein the envelope is modulated by an RF carrier signal to form the first sequence, the method further comprising:

varying a phase of the RF carrier signal during the radiation of the first sequence.

12. The method of claim 1, further comprising:

before radiating the first sequence of RF pulses, radiating a detection sequence.

13. The method of claim 1 further comprising:

delaying to allow polarization of spins to occur between the radiation of the first and second sequences.

14. The method of claim 1, wherein the NMR measurement apparatus is part of a drill string for use with a subterranean well having a borehole, the method further comprising:

producing an axisymmetric static magnetic field having contour lines in the resonance region, the contour lines being substantially straight in a direction that is substantially aligned with an axis of the borehole.

15. The method of claim 14, further comprising:
using the drill string to drill unstabilized.

16. The method of claim 14, further comprising:
using the drill string to drill stabilized.

17. A method for use with an NMR measurement apparatus located in a borehole surrounding an earth formation and subject to relative motion between the apparatus and a sample located in an investigation region of the earth formation, the method comprising;
selecting an initial pulse phase for one or more RF pulses;
using an RF carrier signal to radiate a first sequence of RF pulses, the first sequence comprising two or more pulses, the individual RF pulses having an associated pulse phase;
varying the pulse phase of one or more subsequent RF pulses discretely during the radiation of the first sequence to substantially saturate a first region of the sample;
radiating a second sequence of RF pulses to establish a resonance region within the first region;
detecting an NMR response to the second sequence from the resonance region within the first region; and
measuring an attribute of the sample of the earth formation based on the NMR response.

18. The method of claim 17, wherein the relative motion occurs due to movement of the NMR apparatus.

19. The method of claim 17, further comprising:
varying an envelope of the first sequence during the radiation of the first sequence.

20. The method of claim 17, wherein the NMR measurement apparatus comprises a logging while drilling tool.

21. The method of claim 17, wherein the act of varying the pulse phase comprises:
varying the pulse phase in the first sequence in an uncorrelated manner.

22. The method of claim 17, wherein the act of varying the pulse phase comprises:
slowly varying the pulse phase with respect to durations of RF pulses of the first sequence.

23. The method of claim 17, wherein the NMR measurement apparatus is part of a drill string for use with a subterranean well having a borehole, the method further comprising:
producing an axisymmetric static magnetic field having contour lines in the resonance region, the contour lines being substantially straight in a direction that is substantially aligned with an axis of the borehole.

24. The method of claim 23, further comprising:
using the drill string to drill unstabilized.

25. The method of claim 23, further comprising:
using the drill string to drill stabilized.

26. A method for use with an NMR measurement apparatus located in a borehole surrounding an earth formation subject to relative motion between the apparatus and a sample located in an investigation region of the earth formation, comprising:
radiating a sequence of RF pulses; including at least one refocusing pulse to produce at least one echo from a resonance region of the sample;
radiating additional RF pulses in the sequence to cause a saturation region that is larger than the resonance region, wherein the increased size of the saturation region is due to the motion of the NMR measurement apparatus during radiation of the additional RF pulses; and
detecting an NMR response of the earth formation to the RF pulses and the additional RF pulses of the sequence.

27. The method of claim 26 wherein the sequence has an envelope modulated by an RF carrier signal and further comprising the step of varying the envelope for the additional RF pulses.

28. The method of claim 26, wherein the sequence comprises a CPMG sequence.

29. The method of claim 26, further comprising:
using the sequence as a detection sequence.

30. An NMR measurement apparatus located in a borehole surrounding an earth formation and subject to relative motion between the apparatus and a sample located in an investigation region of the earth formation, comprising:
at least one magnet furnishing a magnetic field;
a coil; and
a pulse generator coupled to the coil and configured to:
select a set of initial RF pulse characteristics defining one or more RF pulses;
radiate a first sequence of RF pulses that substantially saturate a first region in the sample, the first sequence comprising two or more RF pulses having an envelope, the envelope defined by RF pulse characteristics associated with individual RF pulses, the RF pulse characteristics selected from the group including, amplitude, phase, duration and time interval between RF pulses;
vary one or more of the RF pulse characteristics of the envelope within the first sequence with time that substantially saturate the first region of the sample;
radiate a second sequence of RF pulses that establish a resonance region within the first region;
detect an NMR response to the second sequence from the resonance region within the first region; and
measure an attribute of the sample of the earth formation based on the NMR response.

31. The NMR measurement apparatus of claim 30, wherein the pulse generator varies the RF pulse characteristic by slowing varying the duration with respect to individual RF pulses in the first sequence.

32. The NMR measurement apparatus of claim 30, wherein the pulse generator varies the RF pulse characteristics of said RF pulses in the first sequence in an uncorrelated manner.

33. The NMR measurement apparatus of claim 30, wherein the coil receives spin-echoes from the resonance region.

34. An NMR measurement apparatus located in a borehole surrounding an earth formation and subject to relative motion between the apparatus and a sample located in an investigation region of the earth formation, comprising:
at least one magnet furnishing a magnetic field;
a coil; and
a pulse generator coupled to the coil and configured to:
select an initial pulse phase of one or more RF pulses;
utilize an RF carrier signal radiating a first sequence of RF pulses, the first sequence comprising two or more pulses, the individual RF pulses having an associated pulse phase;
vary the pulse phase of one or more subsequent RF pulses discretely during the radiation of the first sequence, which substantially saturates a first region of the sample;
radiate a second sequence of RF pulses establishing a resonance region within the first region;
detect an NMR response to the second sequence from the resonance region within the first region; and measure an attribute of the sample of the earth formation based on the NMR response.

35. The NMR measurement apparatus of claim 34, wherein the pulse generator varies the pulse phase by slowing varying the pulse phase with respect to the duration of RF pulses in the first sequence.

36. The NMR measurement apparatus of claim 34, wherein the pulse generator varies the pulse phase in the first sequence in an uncorrelated manner.

37. The NMR measurement apparatus of claim 34, wherein the coil receives spin-echoes from the resonance region.

38. An NMR measurement apparatus located in a borehole surrounding an earth formation subject to relative motion between the apparatus and a sample located in an investigation region of the earth formation, comprising:

a magnet;

a coil; and a pulse generator coupled to the coil configured to:
   radiate a sequence of RF pulses, including at least one refocusing pulse that produces at least one echo from a resonance region of the sample;
   radiate additional RF pulses in the sequence that cause a saturation region larger than the resonance region, wherein the increased size of the saturation region is due to the motion of the NMR measurement apparatus during the radiation of the additional RF pulses; and
   detect an NMR response of the earth formation to the RF pulses and the additional RF pulses of the sequence.

39. The NMR measurement apparatus of claim 38, wherein the sequence comprises a CPMG sequence.

40. A method for use with an NMR measurement apparatus located in a borehole surrounding an earth formation subject to relative motion between the apparatus and a sample located in an investigation region of the earth formation, comprising:

radiating a sequence of RF pulses, including at least one refocusing pulse to produce at least one echo from a resonance region of the sample;

selecting a set of initial RF pulse characteristics and phase defining one or more additional RF pulses in the sequence;

radiating additional RF pulses in the sequence to cause saturation of a region larger than the resonance region to accommodate the motion of the NMR measurement apparatus, the second sequence having an envelope modulated by an RF carrier, the envelope defined by RF pulse characteristics and a phase associated with individual RF pulses;

wherein at least one of the set of initial RF pulse characteristics and phase of the envelope is varied in an uncorrelated manner for one or more subsequent RF pulses within the sequence; and detecting an NMR response of the earth formation to the RF pulses and the additional RF pulses.

41. The method of claim 40, wherein a spacing between the additional RF pulses is substantially less than a free evolution time.

42. The method of claim 40, wherein a spacing between the additional RF pulses is substantially zero.

43. The method of claim 40, wherein a spacing between the additional RF pulses is substantially set by rise and fall times of the additional RF pulses.

44. The method of claim 40, wherein a duration of each of the additional RF pulses indicates a flip angle, the flip angle being less than about 180 degrees.

45. The method of claim 44, wherein the flip angle is less than about 40 degrees.

46. The method of claim 44, wherein the flip angle is less than about 30 degrees.

* * * * *